United States Patent [19]
Lentzen et al.

[11] Patent Number: 5,714,473
[45] Date of Patent: Feb. 3, 1998

[54] USE OF FLAVOLIGNANS AS ADJUVANTS IN TUMOUR THERAPY

[75] Inventors: Hans Lentzen, Rösrath; Ulrich Mengs, St. Augustin 1; Karl-Peter Odenthal, Grevenbroich; Hilmar Stolte, Bad Oeynhausen, all of Germany

[73] Assignee: Madaus AG, Cologne, Germany

[21] Appl. No.: 377,561

[22] Filed: Jan. 24, 1995

[30] Foreign Application Priority Data

Jan. 24, 1994 [DE] Germany .......................... 44 01 902.5

[51] Int. Cl.⁶ .......................... A61K 31/19; A61K 31/36
[52] U.S. Cl. .............................................. 514/22; 514/574
[58] Field of Search ........................ 514/22, 574

[56] References Cited

U.S. PATENT DOCUMENTS 4,871,763  10/1989  Madaus et al. .......................... 517/45.2

FOREIGN PATENT DOCUMENTS 1923082  11/1970  Germany .
3533656  5/1986  Germany .

OTHER PUBLICATIONS

Abraham et al., "The Structure of Silydianin, an Isomer of Silymarin (Silybin)", by X–ray Analysis, Tetrahedron LTRS. No. 31, pp. 2675–2678, 1970.

Pelter et al., "The Structure of Silybin (Silybum Substance E6)", The First Flavonolignan, Tetrahedron LTRS. No. 25, pp. 2911–2916, 1968.

H. Wagner et al., "The Structure of Silychristin", A Second Silymarin Isomer From Silybum Marianum Tetrahedron LTRS. No. 22, pp. 1895–1899, 1971.

Physicians' Desk Reference, 48th Edition 1994 pp. 458–461, 666–669, Medical Economics Data Production Company, Montvale, N.J. (Dec. 1993).

CA 103:32031, Miyazaki et al. (1985).

CA 91:84686, Vogel et al. (1979).

Primary Examiner—Jeffrey C. Mullis
Attorney, Agent, or Firm—Felfe & Lynch

[57] ABSTRACT

The present invention is concerned with the use of flavolignans as adjuvants in the case of chemotherapeutic tumour treatment and for the protection of cells in the urogenital region.

2 Claims, 11 Drawing Sheets

USE OF FLAVOLIGNANS AS ADJUVANTS IN TUMOUR THERAPY

BACKGROUND OF THE INVENTION

The present invention is concerned with the use of a flavolignan as adjuvant in the case of chemotherapeutic tumour treatment and for the protection of cells in the urogenital region.

Flavolignans are pharmacologically active polyhydroxyphenylchromanone compounds which are chemically bound to coniferyl alcohol, the best known representative of which is silymarin. Silymarin is a mixture of polyhydroxyphenolchromanones which is obtainable by the extraction of the fruit of Mary's thistle (Silybum marianum Gaertn.) (see, for example DE-A-19 23 082). The components of the silymarin mixture are silibinin, silidianin and silichristin (cf. DE-A-1 923 082, as well as Tetrahedron Letters, 25, 2911, 1968; Tetrahedron Letters, 31, 2675–2678/1970; and Tetrahedron Letters, 22, 1895–1899/1971). The most important component is silibinin, which has the following structural formula:

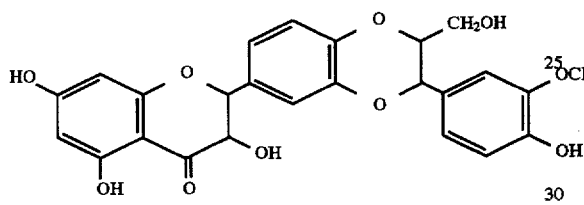

Silymarin and silibinin are valuable liver therapeutics (see, for example, DE-A-19 23 082 and DE-A-35 37 656).

SUMMARY OF THE INVENTION

Surprisingly, we have now found that silymarin and the individual components thereof can be used as adjuvants in tumour therapy and for the protection of the cells in the urogenital region.

Therefore, a subject of the present invention is the use of at least one flavolignan as adjuvant in the case of the chemotherapeutic treatment of tumour diseases and for the protection of cells in the urogenital region.

For this purpose, it is preferred to use silymarin or one or more components thereof. Silibinin, especially in the form of its dihemisuccinate salt, has thereby proved to be especially useful.

Furthermore, it has been shown that the mentioned flavolignans offer an outstanding protection against damages which are regularly brought about by tumour therapeutics. Therefore, the compounds used according to the present invention can be used as adjuvants in the treatment of tumours with chemotherapeutics, for example cyclophosphamide, methotrexate, vincristine, vinblastine, doxorubicin, bleomycin, mitomycin, etoposide, teniposide and especially carboplatin, cisplatin and adriamycin and derivatives thereof.

Surprisingly, we have found that the anti-tumour action of chemotherapeutics is not influenced by the compounds used according to the present invention.

BRIEF DESCRIPTION OF THE DRAWINGS

FIG. 1 illustrates the progression of the body weight in accordance with this invention FIG. 2 illustrates effect on the creatnine clearance FIG. 3 illustrates effect on the proteinuria FIG. 4 illustrates fibronectin excretion per 24 hours FIG. 5 illustrates excretion of the enzyme N-acetyl-β-D-glucosainidase in the urine FIG. 6 illustrates excretion of the enzyme alanine-aminopeptidase (AAP) in the urine.

FIG. 7 illustrates fractional magnesium excretion.

FIG. 8 the progression of the body weight

FIG. 9 protein excretion per 24 hours

FIG. 10 fibronectin excretion per 24 hours

FIG. 11 increase of the plasma level of malondialdehyde (MDA); clear bars; immediately before the treatment; cross-hatched bars: 1 hour after the treatment.

FIG. 12 the influencing of the DNA synthesis by cisplatin

FIG. 13 the specific DNA synthesis of the HepG2 cells in the case of cisplatin treatment (experiment I)

FIG. 14 the specific protein synthesis of the HepG2 cells in the case of cisplatin treatment (experiment I)

FIGS. 15 and 16 the specific DNA and protein synthesis; (experiment II)

DETAILED DESCRIPTION OF THE INVENTION AND PREFERRED EMBODIMENTS

Figure 1:
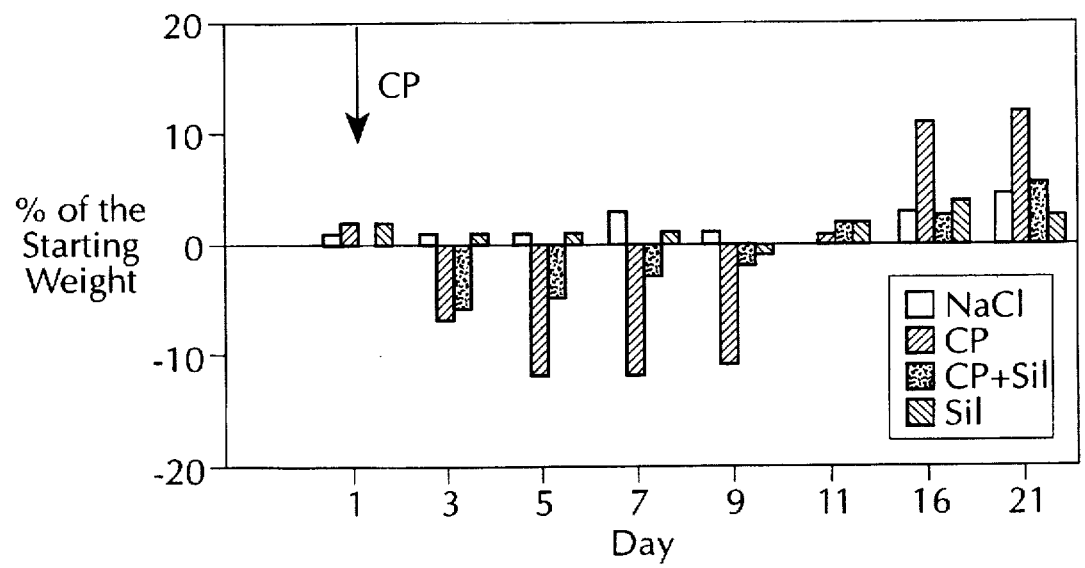
FIGS. 1 to 7 of the accompanying drawings show the results obtained in the case of cisplatin (CP) nephrosis.

As is known, the flavolignans increase the protein biosynthesis in body cells and thereby promote the regeneration thereof. Surprisingly, we have now found that this effect is exerted selectively, i.e. the flavolignans increase the protein biosynthesis only in healthy, intact cells but not in tumour cells. Thus, the proliferation of the tumour cells is not promoted so that a more rapid growth of the tumour cells does not take place.

Furthermore, animal experimental investigation on rats have shown that, by means of the administration of the compounds used according to the present invention, the nephrotoxicity of cytostatics can be clearly reduced. We have ascertained that the flavolignans offer a substantial protection of the glomerular and tubular apparatus so that a protection of the renal parenchyma is achieved.

Therefore, the flavolignans can be used for the accompanying treatment in tumour therapy because, on the one hand, they substantially reduce the nephrotoxicity of the cytostatics used and, on the other hand, they do not impair the action of the cytostatics and do not promote the proliferation of the tumour cells.

Furthermore, we have found that the flavolignans are especially useful for protection against nephrotic damages and for the protection of the tubular and/or glomerular apparatus. The nephro-protective action of the flavolignans is not only to be observed in the case of kidney damages which are brought about by cytostatics but also they extend to kidney damages of any genesis, for example the damages brought about by the toxic action of heavy metals, especially mercury and lead compounds, ischemic damages, inflammatory damages, i.e. nephritides of any origin, including those of bacterial and viral origin, as well as the damages brought about by cytostatics already mentioned. The nephro-protective action of the flavolignans is to be understood as a protective action against the mentioned noxi, the flavolignans themselves causing no kidney damage.

According to an advantageous embodiment of the present invention, the flavolignans are used in combination with at least one alkali metal hydrogen citrate composition or compound or of a hydrate thereof with the molar composition K:Na:H: $(C_6H_5O_7)$=w:x:y:z, wherein w is a whole number of from 0 to 15, x is a whole number of from 0 to 15; y is a whole number from 0 to 3; and z is a whole number from 1 to 5, whereby W+X+y=3; 6; 9; 12 or 15 corresponding to z=1; 2; 3; 4 or 5 and w+X=1 to 15, whereby w=6; x=6; y=3 and z=5 are preferred. These citrates are described in DE-A-43 28 577. By means of the use of the citrates, the nephroprotective effect of the flavolignans is further strengthened.

The compounds used according to the present invention are usually administered in the form of a pharmaceutical agent which contains conventional adjuvant and additive materials. The agents can be administered orally, for example in the form of tablets, dragees, capsules or liquids, or rectally in the form of suppositories, or parenterally, for example intravenously. Silymarin is administered orally. Silibinin can be administered orally, for example in combination with or as a complex with cyclodextrin or phospholipids, for example lecithin, or as methylglucamine or dihemisuccinate salt. The salts can also be used for parenteral administration. The mentioned combinations, complexes and salts are described in EP-A-O 422 497, EP-A-O 209 037, EP-A-O 209 038, DE-A-34 42 639 and DE-A-23 02 593.

The compounds used according to the present invention can be administered prophylactically or for the treatment of damages which have already occurred. As adjuvant in tumour therapies, they can be given before, during or after administration of the tumour chemotherapeutic. The dosaging depends upon the conditions of the individual cases, but, in the case of humans, it is generally in the range of from 200 to 500 mg/day.

The following experiments explain the use of silymarin or of the individual components thereof according to the present invention. It will be understood, however, that the following examples are for illustrative purposes only, and are not intended to limit the spirit and/or scope of the invention in any way.

1. Nephro-protective action of silibinin in the case of cisplatin nephrosis.

The cytostatic cisplatin (CP) is regarded as a model substance for the production of tubular kidney damages.

In order to investigate the protective influence of silibinin-C-2',3'-dihydrogen succinate, disodium salt, female Wistar rats were, in each case, treated as follows:

5 mg/kg KG CP i.v. (n=12)

5 mg/kg KG CP i.v.+200 mg/kg silibinin i.v. as silibinin-C-2',3'-dihydrogen succinate, disodium salt (1 hour before CP administration; n=11)

Two further groups received either only silibinin (n=10) or the vehicle (sodium chloride; n=12) and served as controls. The rats of all groups were regularly investigated over the course of 21 days p.a. with regard to their kidney functions, whereby, in the case of the following parameters, a protective action of silibinin was shown:

Progression of the body weight:

After treatment with CP, there resulted a distinct reduction of the body weight. In the case of pretreatment with silibinin, the loss of weight was distinctly smaller (FIG. 1).

Figure 2:
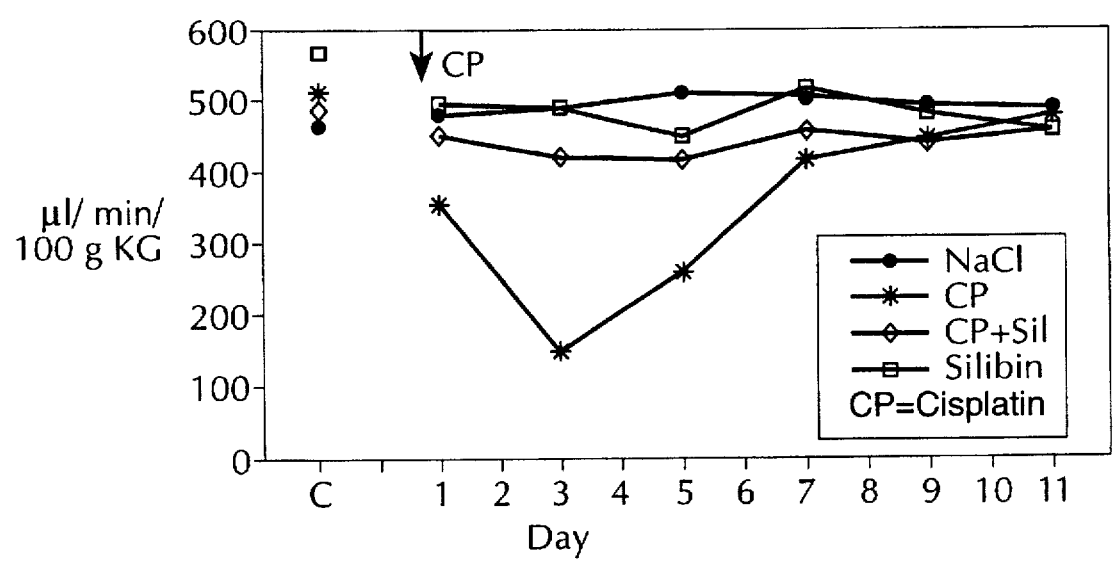

Creatinine clearance:

The glomerular filtrate rate (GFR) was determined via the creatinine clearance. Treatment with CP led to a strong decrease of the GFR. In the case of pretreatment with silibinin, the GFR remained in the normal range. (FIG. 2).

Urea:

Parallel to the limitations in the GFR, after administration of CP, it resulted in an increase of the urea concentration in the serum. By means of pretreatment with silibinin, an increase of the urea values in the serum was prevented.

Figure 3:
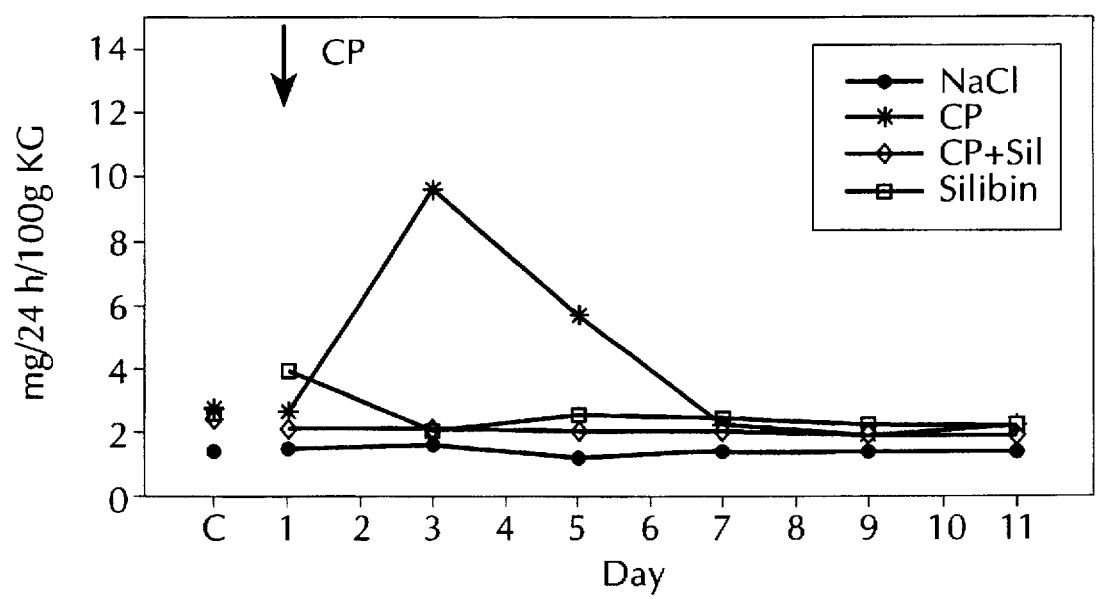

Protein excretion:

Treatment with CP led to an increase of proteinuria. Silibinin prevented this increase (FIG. 3).

Figure 4:
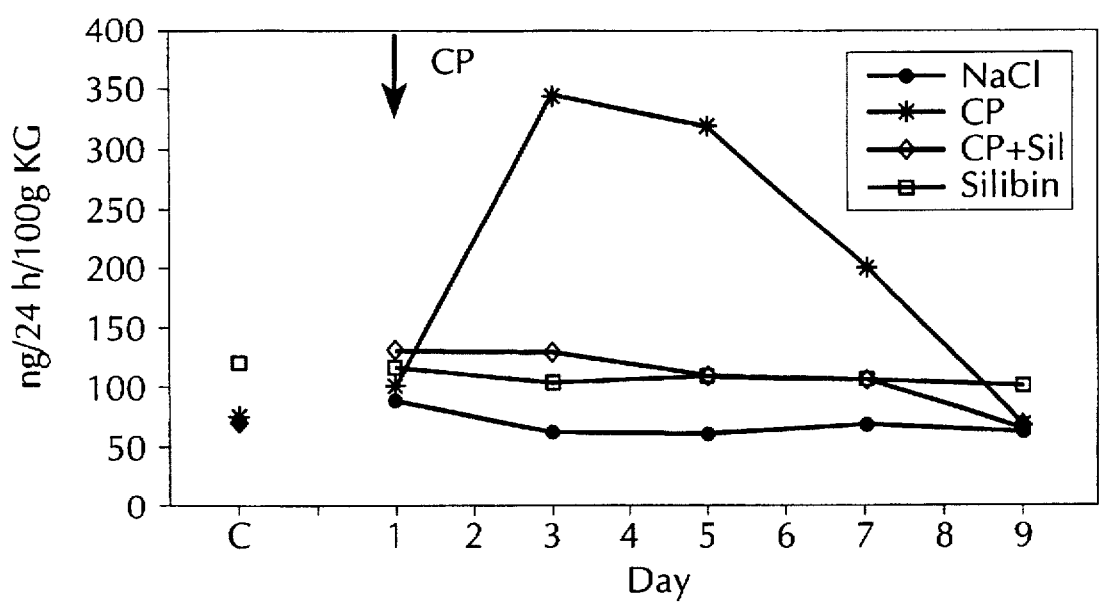

Fibronectin:

The urine concentration of the structure protein fibronectin was significantly increased by treatment with CP. By means of pretreatment with silibinin, the values remained unchanged in comparison with the controls (FIG. 4).

Figure 5:
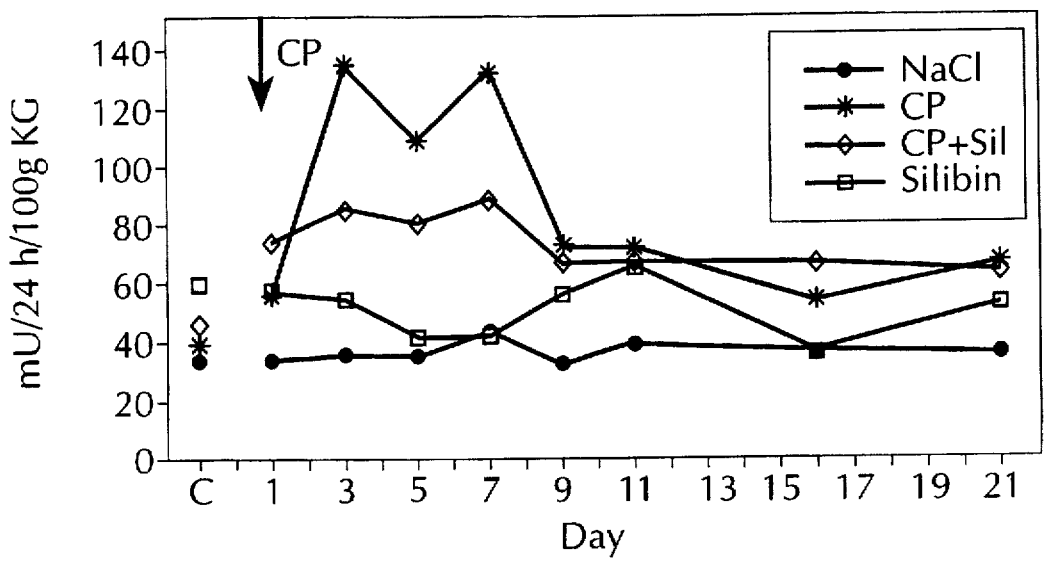

N-acetyl-β-D-glucosaminidase (NAG):

The excretion of the enzyme NAG in the urine was increased after CP administration in comparison with the sodium chloride group. In the case of animals pretreated with silibinin, the NAG values were significantly lower than those of the rats treated with CP (FIG. 5).

Figure 6:
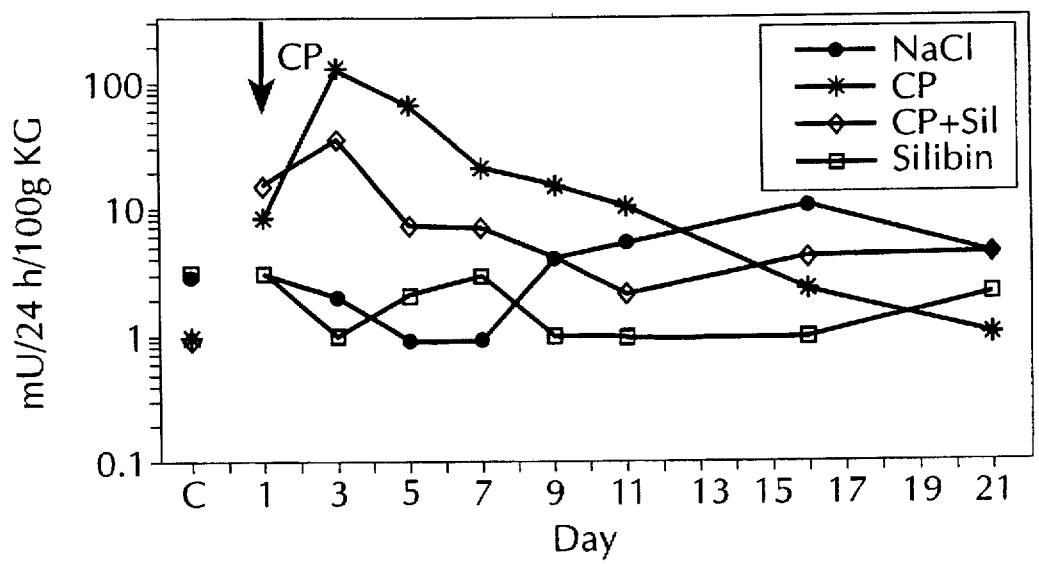

Alanine aminopeptidase (AAP):

There was obtained a picture similar to that in the case of NAG. The CP-induced increase in the urine was significantly smaller in the case of pretreatment with silibinin (FIG. 6).

Figure 7:
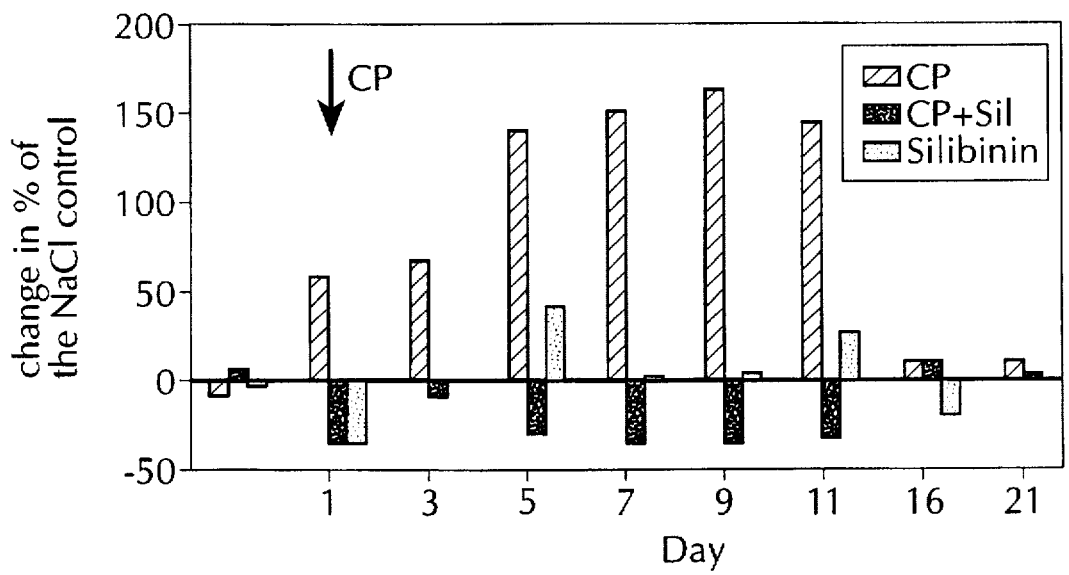

Magnesium:

In the case of CP-treated rats, it resulted in a significant increase of the magnesium excretion. In the case of the silibinin+CP group, this effect could not be ascertained (FIG. 7).

Histopathology:

In the case of histological assessment, in the case of the CP-treated rats, there were found massive necroses of the renal tubuli. In the case of the additional administration of silibinin, only individual tubuli epithelial cells with degenerative changes were observed.

Thus, in the case of the nepthrosis induced by CP, the parameters mentioned in the following were favourably influenced by silibinin. There was found:

smaller loss of body weight no reduction of the creatinine clearance no increase of the urea values in the serum no proteinuria lesser fibronectinuria lower enzymuria (NAG, AAP)

no renal magnesium loss distinctly reduced histopathological changes

2. Nephroprotective action of silibinin in the case of adriamycin nephrosis

The cytostatic adriamycin (ADR) is regarded as a model substance for the production of a glomerular-toxic nephropathy. In order to investigate the influence of silibinin-C-2',3'-dihydrogen succinate, disodium salt (silibinin dihemisuccinate) on the ADR renal toxicity, female Wistar rats were treated as follows:

5 mg/kg ADR i.v. (n=12)

5 mg/kg ADR i.v.+200 mg/kg silibinin i.v. as silibinin-C-2'3'-dihydrogen succinate, disodium salt (1 hour before the ADR administration, n=12).

In addition, in each case one group was only treated with silibinin (n=6) or with the vehicle (sodium chloride; n=6) and served as controls.

Figure 8:
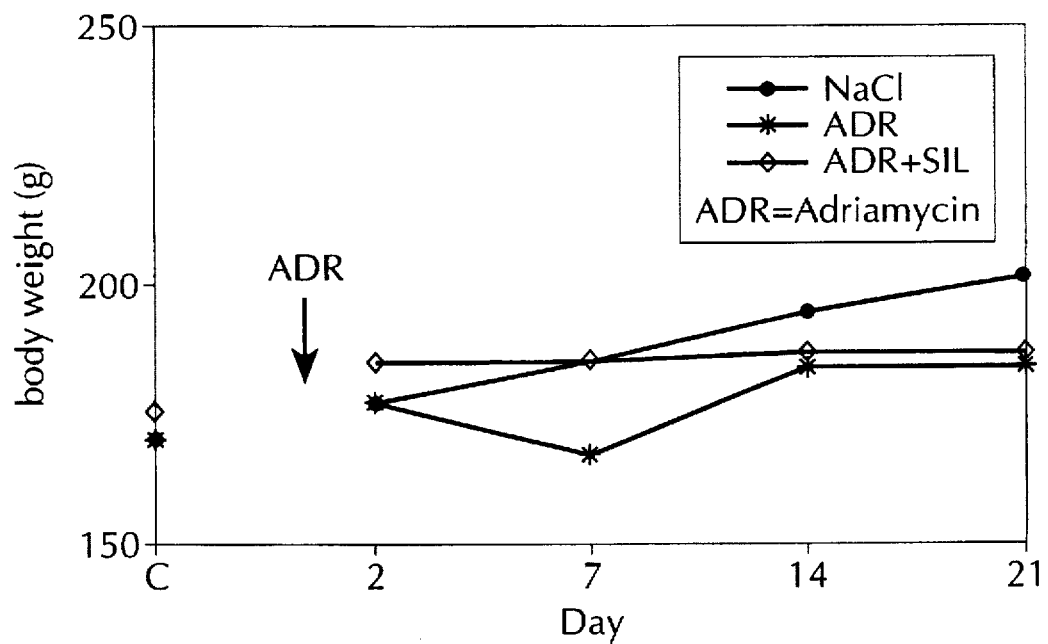
FIGS. 8 to 11 illustrate the results in the case of adriamycin nephrosis as indicated.

The rats were investigated up to the 21st day with regard to the kidney functions. The following parameters were favourably influenced by silibinin:

Progression of the body weight:

Treatment with ADR led to a progressive weight loss. This effect was substantially compensated for by treatment with silibinin (FIG. 8).

Figure 9:
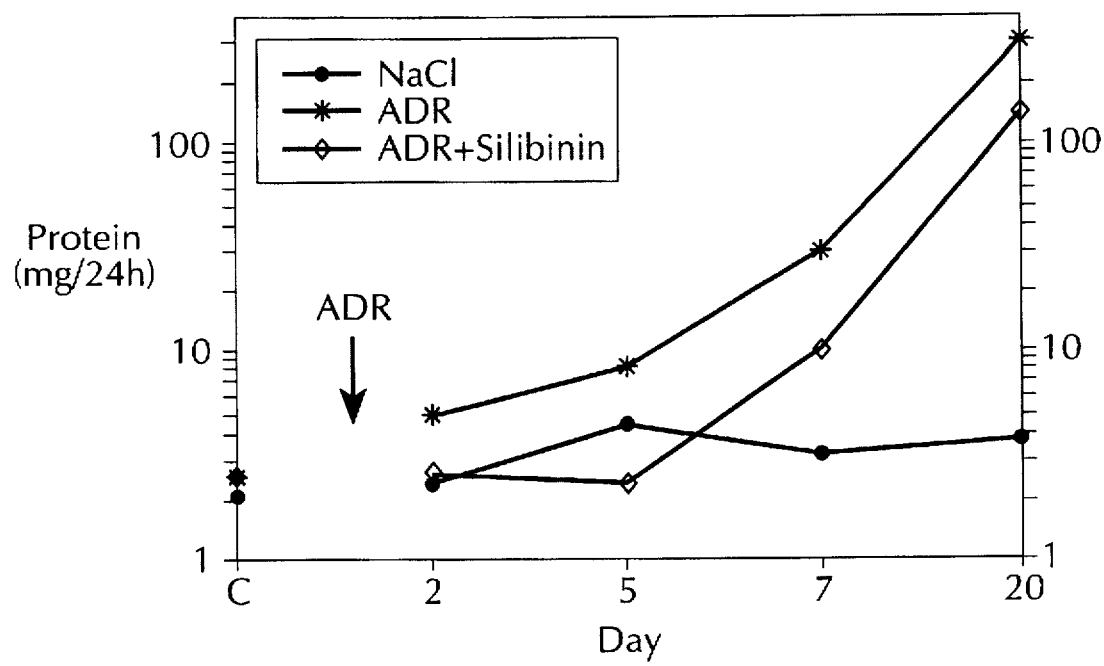

Protein excretion:

ADR led to a distinct increase of the proteinuria. The rats of the silibinin+ADR group also showed an increase but at different points of time remained significantly below the values of the ADR group (FIG. 9).

Figure 10:
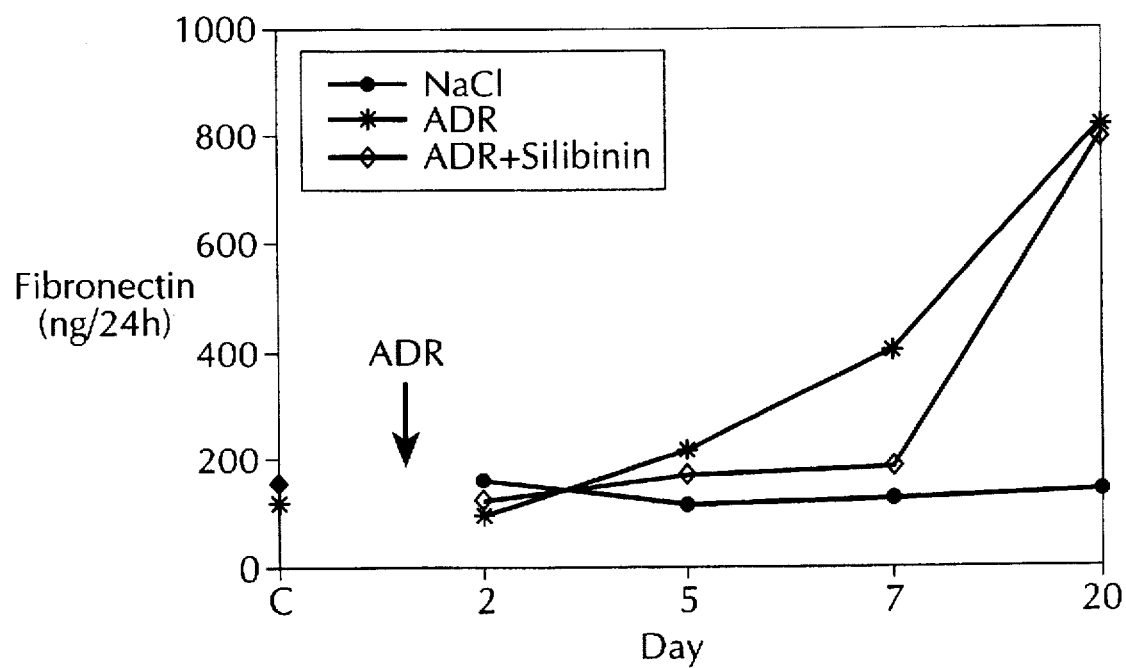

Fibronectin:

After ADR administration, the fibronectin excretion increased distinctly. The occurrence of this effect was delayed in the case of rats pretreated with silibinin (FIG. 10).

Figure 11:
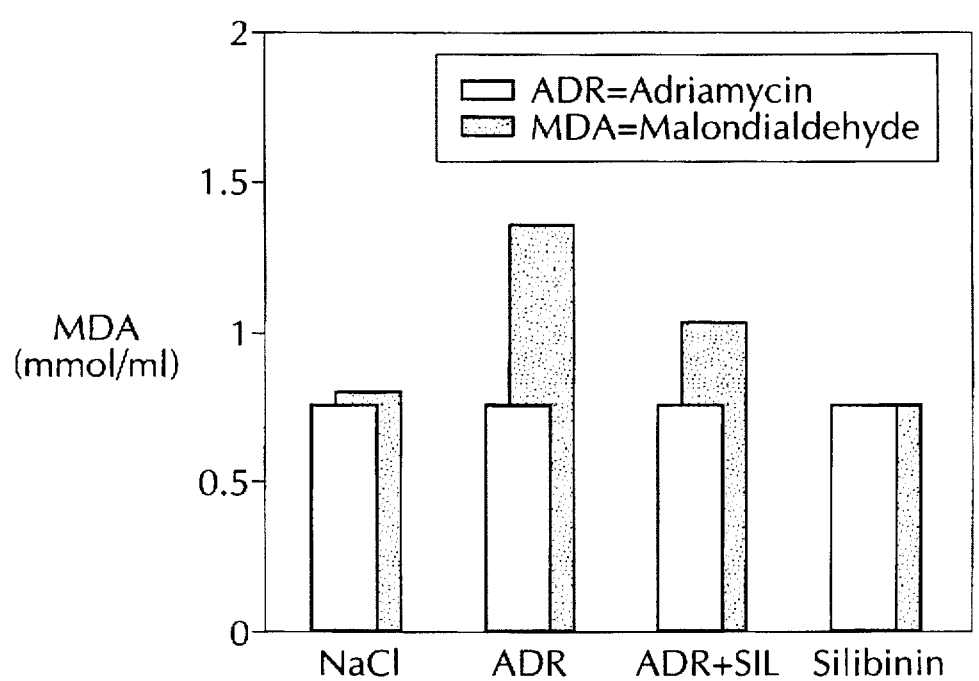
Figure 12:
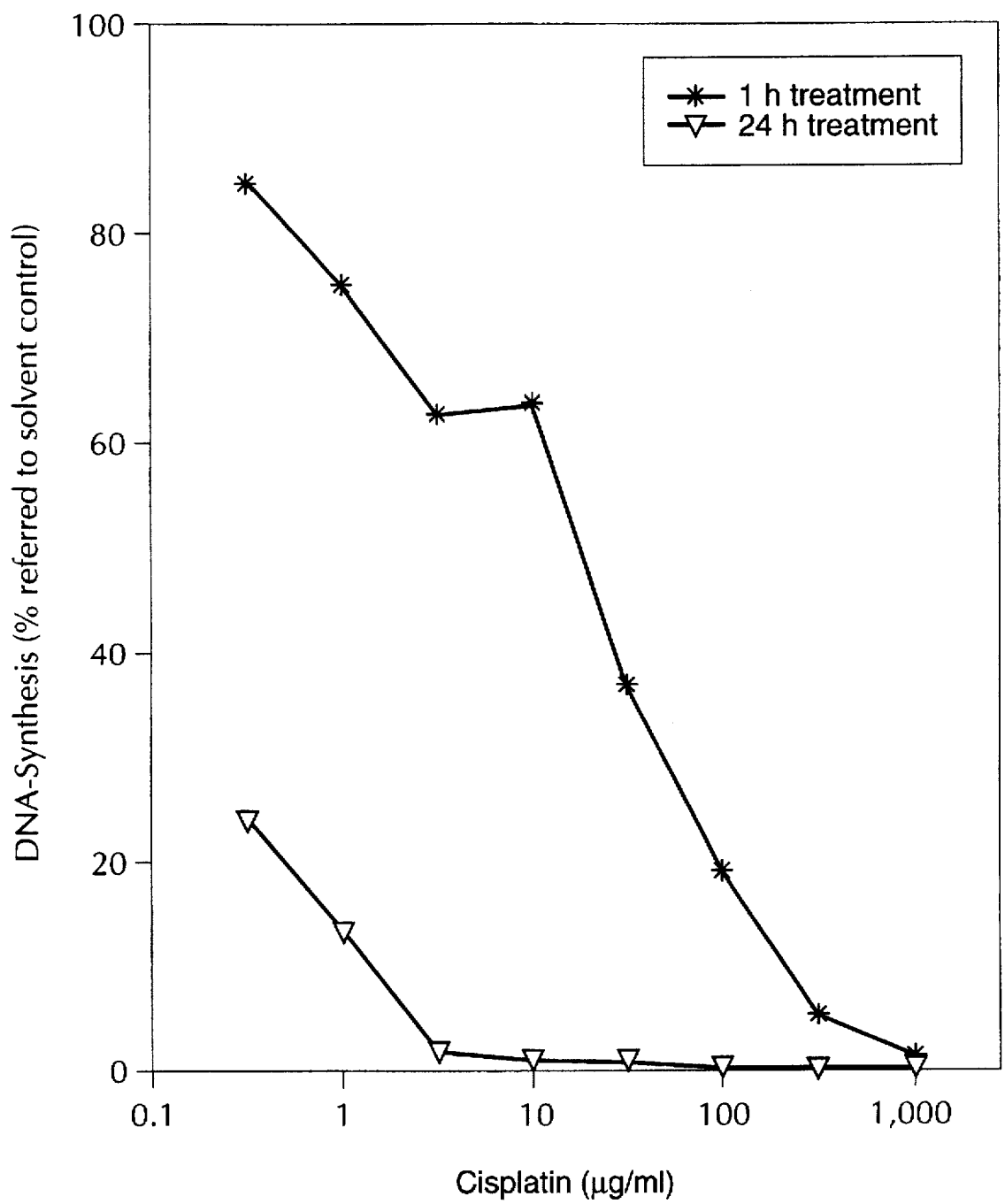
FIGS. 12 to 16 illustrate the influencing of the DNA and protein synthesis in the case of cisplatin treatment as indicated.
Figure 13:
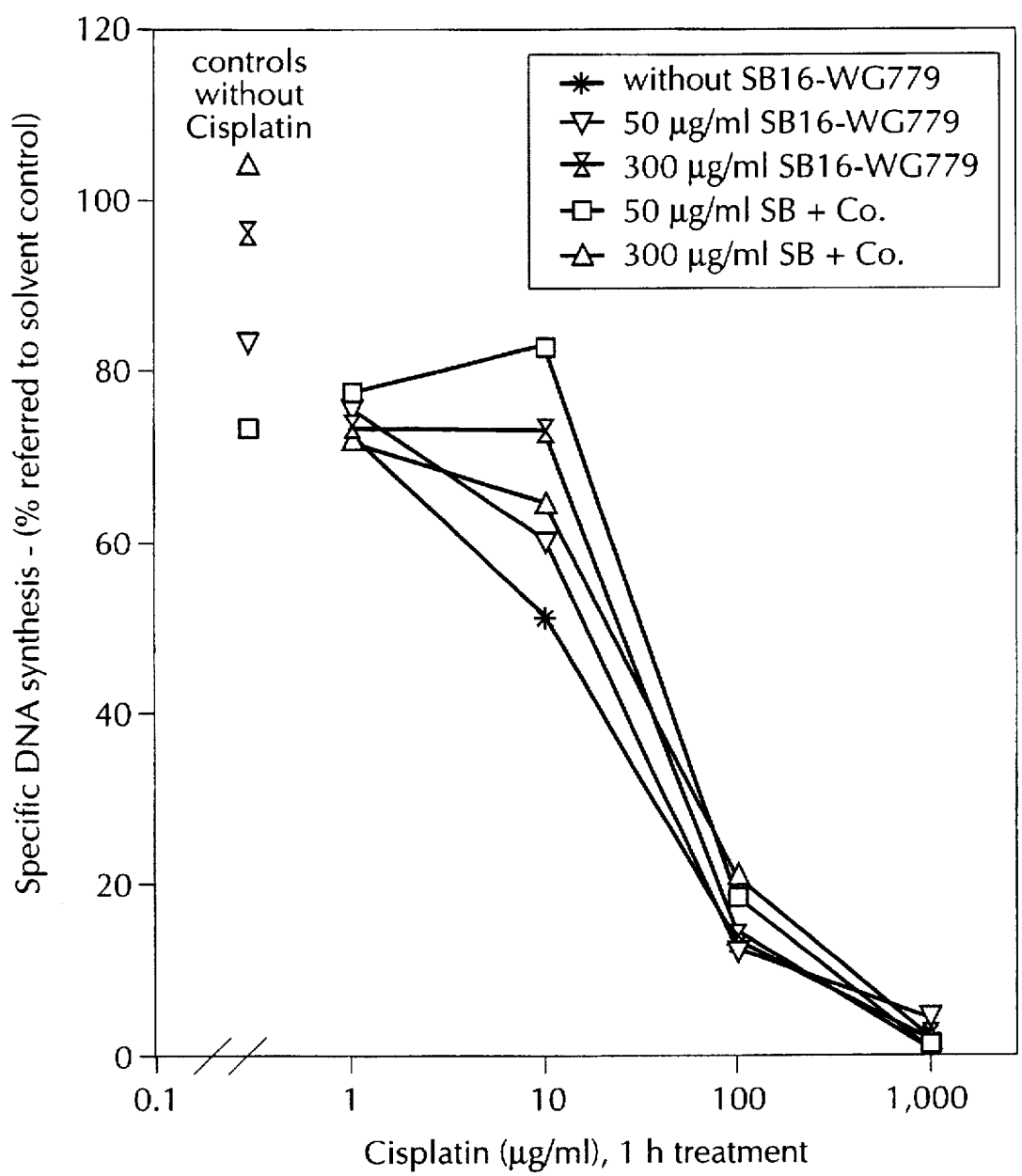
Figure 14:
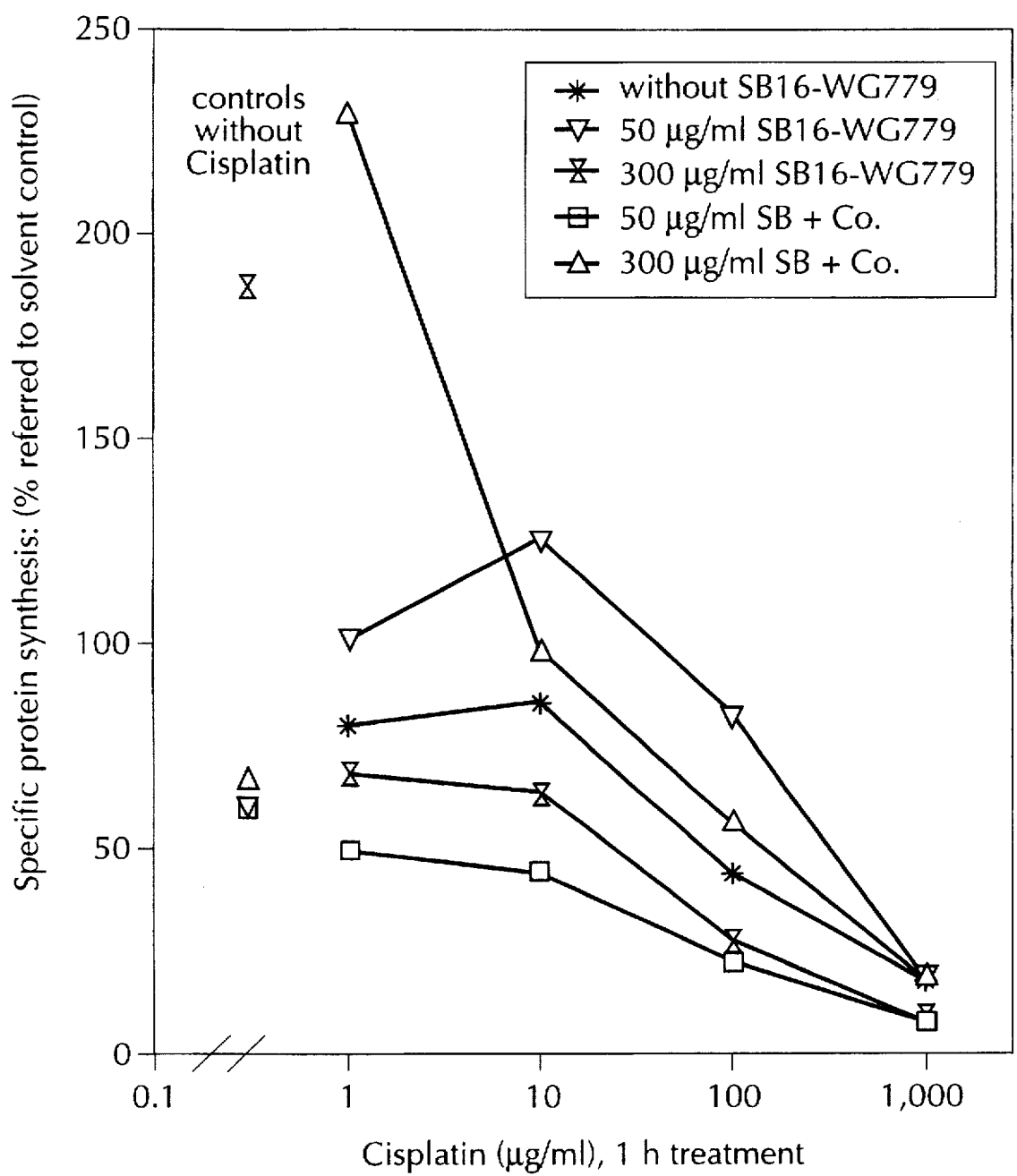
Figure 15:
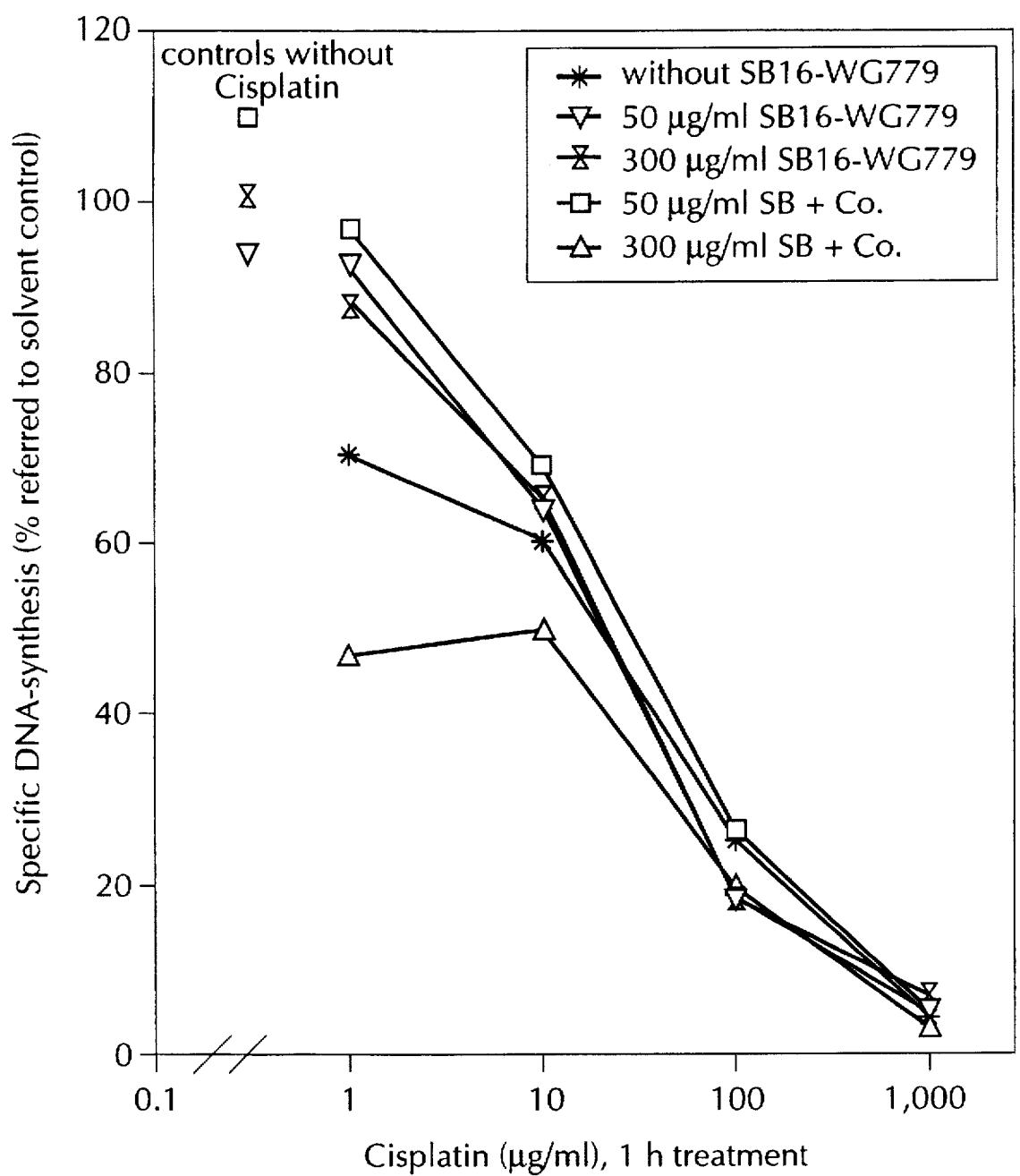
Figure 16:
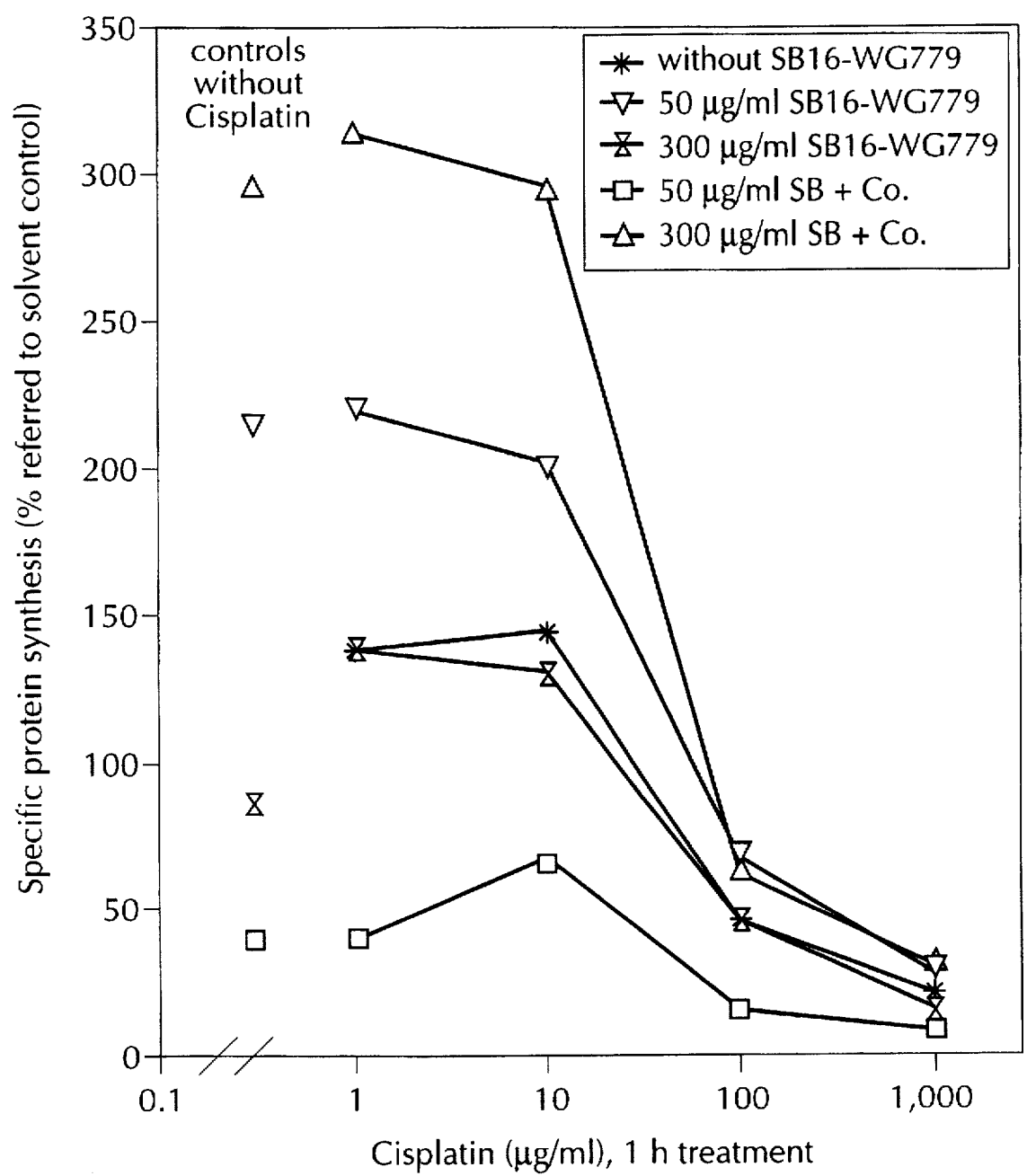

Malondialdehyde:

After administration of ADR, in all groups it resulted in a significant increase of the plasma level for malondialdehyde. However, in the group additionally treated with silibinin, this was distinctly lower (FIG. 11).

Thus, in the case of the nephrosis induced by ADR, by means of pretreatment with silibinin the following parameters could be favourably influenced. There was found:

- smaller body weight loss
- smaller proteinuria
- smaller fibronectinuria
- smaller plasma level for malondialdehyde 3. Nephroprotection by silibinin in the case of rats with toxic nephrosis brought about by mercuric chloride In order to investigate the protective action of silibinin (silibinin-C-2',3'-dihydrogen succinate, disodium salt) in the case of mercuric chloride mephropathy, female Wistar rats were treated as follows:

0.5 mg/kg mercuric chloride i.p. (n=10)

0.5 mg/kg mercuric chloride i.p.+200 mg/kg silibinin i.v. (30 minutes before administration of mercuric chloride; n=10).

Before the treatment and on the 2nd day p.a., blood and urine investigations were carried out. On the 3rd day p.a., the animals were dissected and the kidneys investigated histologically. In the case of the following parameters, there was thereby obtained a protective action by silibinin:

Creatinine:

By means of the administration of mercuric chloride, the creatinine values in the plasma were distinctly increased. In the case of rats pretreated with silibinin, the increase was smaller (see the following Table 1).

Malate dehydrogenase (MDH):

Treatment with mercuric chloride led to an increase of the MDH in the urine. In the silibinin group, this was distinctly less marked (see the following Table 1).

Gamma-glutamyl transferase (γ-GT):

In the urine of animals treated with mercuric chloride, strongly increased γ-GT activities were measured. On the other hand, in the case of animals pretreated with silibinin, only a low degree increase was ascertained (see the following Table 1).

Lactate dehydrogenase (LDH):

Similarly to the case of MDH and γ-GT, the enzyme increase of LDH in urine induced by mercuric chloride is distinctly reduced by a pretreatment with silibinin (see the following Table 1).

Glucosuria:

After administration of mercuric chloride, a massive increase of the glucose excretion was ascertained. In the case of rats pretreated with silibinin, the glucose concentrations in the urine were significantly lower (see the following Table 1).

Histopathology:

In the case of the histological assessment, in the kidneys of the rats treated with mercuric chloride there were found clear indications of a tubular degeneration up to necrosis. The changes in rats pretreated with silibinin were distinctly less marked.

Thus, by means of a pretreatment with silibinin, the development of toxic nephropathy induced with mercuric chloride could be favourably influenced. There were found:

- reduced increase of the creatinine plasma level
- reduced enzymuria (MDH, γ-GT, LDH)
- significantly reduced glucosuria
- histologically distinctly less tubule damages.

TABLE 1

Influence of silibinin on the mercuric chloride nephropathy in rats (average value ± standard deviation; n = 10).

| parameter | experimental day | $HgCl_2$ | $HgCl_2$ + silibinin |
|---|---|---|---|
| creatinine in the plasma (μmol/l) | −3 | 39.8 ± 3.22 | 37.1 ± 3.41 |
|  | 2 | 51.8 ± 15.68 | 42.7 ± 8.98 |
| MDH in the urine (U/V16h) | −3 | 0.27 ± 0.085 | 0.24 ± 0.079 |
|  | 2 | 3.96 ± 8.091 | 1.98 ± 4.863 |
| γGT in the urine (U/V16h) | −3 | 5.02 ± 3.75 | 3.75 ± 1.228 |
|  | 2 | 11.51 ± 15.996 | 6.90 ± 5.824 |
| LDH in the urine (U/V16h) | −3 | 0.071 ± 0.0437 | 0.057 ± 0.0477 |
|  | 2 | 1.511 ± 2.3390 | 1.055 ± 2.7200 |
| glucose in the urine (μmol/V16h) | −3 | 4.23 ± 1.363 | 3.55 ± 0.494 |
|  | 2 | 72.98 ± 86.855 | 9.76 ± 20.220 |

4. Modulation of the cisplatin-mediated cytotoxicity on HepG2 human tumour cells As shown above, silibinin possesses nephro-protective activity with regard to the nephrotoxicity of cisplatin, adriamycin and mercuric chloride. In the case of tumour therapy by means of cytostatics, an impairment of the cytostatic action by means of the adjuvant used according to the present invention would be just as undesirable as the promotion of the tumour growth by the adjuvant. In order to investigate this, the possible modulation of the cisplatin-mediated cytotoxicity by silibinin on HepG2 human tumour cells was investigated in vitro.

HepG2 tumour cells are sensitive indicators of the cisplatin-mediated cytotoxicity and are, therefore, suitable as an in vitro model in order to demonstrate a modulation of the cytostatic effect of cisplatin.

In order to investigate the effect of silibinin on the cytostatic action of cisplatin, the growth of the tumour cells was monitored by measuring the DNA synthesis by incorporation of $^3$H-thymidine into the cellular DNA.

The total protein synthesis in the cells was measured by the incorporation of $^3$H-leucine and in order to be able to determine whether silibinin possesses an undesired stimulating activity on the protein synthesis of the tumour cells.

The silibinin was used in the form of the disodium silibinin dihemisuccinate (in the following briefly referred to as silibinin), dissolved in dimethyl sulphoxide. The controls were carried out with the use of untreated (negative) controls, solvent controls (medium containing 1% dimethyl sulphoxide), silibinin without cisplatin and cisplatin without silibinin.

In order to ascertain whether a direct interaction is present between silibinin and cisplatin, there was also provided a co-incubation of both substances after the silibinin preincubation.

After ending of both treatment periods, there was determined either the DNA synthesis or the total protein synthesis.

Two independent experiments were carried out for both end points.

DNA synthesis:

During the silibinin treatment period, all cells were labelled with 5 mCi/ml $^{14}$C-thymidine which served as parameter for the number of adherent cells. The cells were then washed twice with RPMI and treated for one hour with cisplatin. Subsequently, the cells were washed with RPMI and fed with 200 µl of medium which contained 2.6 µCi/ml $^3$H-thymidine (0.5 µCi/culture). After radio-active labelling for one hour, the cells were harvested as described above.

The incorporated amount of $^3$H and $^{14}$C was determined by liquid scintillation counting. The $^3$H/$^{14}$C ratio was calculated in order to obtain the DNA synthesis corrected with regard to the cell count. This ratio is designated as specific DNA synthesis.

Total protein synthesis:

2.5×10$^5$ HepG2 cells/culture were treated in 24 well plates with silibinin and cisplatin as described above for the DNA synthesis. After washing with RPMI, the cells were fed with RPMI which was supplemented with 10% FCS. Subsequently, 0.5 µCi/ml $^3$H-leucine were immediately added thereto per well in order to label the newly synthesised cell protein. After labelling for two hours, the medium was sucked off and the monolayer was washed with PBS. The cell content was liberated by the addition of 1 ml 0.1% Nonidet NP 40 in PBS and with vigorous shaking for 30 minutes.

200 µl portions were used for the protein determination after staining with Biorad colour reagent at 595 nm, with the use of spectral photometer. The 500 µl portions were transferred into polypropylene centrifuge tubes, 500 µl of ice-cold 60% trichloroacetic acid (TCA) were added thereto and the acid-insoluble material was precipitated for 30 minutes at 4° C. After centrifuging for 10 minutes at 4000 r.p.m., the pellet obtained was washed with 30% TCA at 4° C. and solubilised for at least 10 minutes with 0.5 ml of a 0.3N sodium hydroxide solution at 60° C. The solution was then neutralised with 0.1 ml of 0.1N hydrochloric acid.

The incorporated amount of $^3$H-leucine was determined by liquid scintillation counting. The $^3$Hdpm/OD$_{595}$ value was calculated in order to obtain the total protein synthesis with regard to the cell count.

The following concentrations were chosen for the experiments:

silibinin pretreatment: 50.00 and 300.00 µg/ml cisplatin: 1.00; 10.00; 100.00 and 1000.00 µg/ml In both experiments, the preincubation with silibinin gave rise to no impairment on the basis of the DNA synthesis of the HepG2 cell-determined cytostatic activity of cisplatin.

The treatment with 50 µg/ml or 300 µg/ml silibinin alone increased neither the DNA synthesis nor the protein synthesis of the HepG2 cells used. This shows that silibinin possesses no properties activating the tumour cells.

Summarising, it is, therefore, to be ascertained that silibinin displays neither an undesired inhibiting effect on the cytotoxicity of cisplatin nor an undesired stimulating activity on the HepG2 cells.

The results obtained are summarised in the following Tables 2 and 3 and in FIGS. 12 to 16 of the accompanying drawings.

TABLE 2

Main experiment: DNA Synthesis

| SB16-WG779 [µg/ml] | cisplatin [µg/ml] | Experiment I $^3$H/$^{14}$C$^1$ | % referred to solvent control | Experiment II $^3$H/$^{14}$C$^1$ | % referred to solvent control |
|---|---|---|---|---|---|
| — | 0.0 | 2.99$^2$ | 100 | 2.79$^2$ | 100 |
| — | 1.0 | 2.17 | 73 | 1.93 | 69 |
| — | 10.0 | 1.54 | 52 | 1.67 | 60 |
| — | 100.0 | 0.43 | 14 | 0.70 | 25 |
| — | 1000.0 | 0.10 | 3 | 0.12 | 4 |
| — | 0.0 | 2.99$^2$ | 100 | 2.79$^2$ | 100 |
| 50.0 | 0.0 | 2.48 | 83 | 2.57 | 92 |
| 50.0 | 1.0 | 2.24 | 75 | 2.55 | 91 |
| 50.0 | 10.0 | 1.83 | 61 | 1.79 | 64 |
| 50.0 | 100.0 | 0.39 | 13 | 0.52 | 19 |
| 50.0 | 1000.0 | 0.14 | 5 | 0.13 | 5 |
| — | 0.0 | 2.99$^2$ | 100 | 2.79$^2$ | 100 |
| 300.0 | 0.0 | 2.87 | 96 | 2.52 | 90 |
| 300.0 | 1.0 | 2.18 | 73 | 2.20 | 79 |
| 300.0 | 10.0 | 2.17 | 73 | 1.66 | 59 |
| 300.0 | 100.0 | 0.46 | 15 | 0.47 | 17 |
| 300.0 | 1000.0 | 0.06 | 2 | 0.17 | 6 |
| — | 0.0 | 3.66$^3$ | 100 | 2.89 | 100 |
| 50.0* | 0.0* | 2.69 | 73 | 3.19 | 110 |
| 50.0* | 1.0* | 2.83 | 77 | 2.81 | 97 |
| 50.0* | 10.0* | 3.03 | 83 | 2.01 | 70 |
| 50.0* | 100.0* | 0.68 | 19 | 0.77 | 27 |
| 50.0* | 1000.0* | 0.09 | 2 | 0.15 | 5 |
| — | 0.0 | 3.66$^3$ | 100 | 2.89 | 100 |
| 300.0* | 0.0* | 3.82 | 104 | ** | ** |
| 300.0* | 1.0* | 2.65 | 72 | 1.36 | 47 |
| 300.0* | 10.0* | 2.38 | 65 | 1.44 | 50 |
| 300.0* | 100.0* | 0.82 | 22 | 0.59 | 20 |
| 300.0* | 1000.0* | 0.11 | 3 | 0.09 | 3 |

$^1$ = specific DNA synthesis, average value of 3 cultures
$^2$ = average value of 9 cultures
$^3$ = average value of 6 cultures
\* = 24 h. pretreatment with SB16-WG779 + 1 hr. co-incubation with SB16-WG779 and cisplatin
\*\* = could not be evaluated
SB16-WG779 = silibinin-C-2',3-dihydrogen succinate, disodium salt (silibinin dihemisuccinate)

TABLE 3

Main experiment: Protein Synthesis

| SB16-WG779 [µg/ml] | cisplatin [µg/ml] | Experiment I $^3$H/OD$_{595}$$^1$ | % referred to solvent control | Experiment II $^3$H/OD$_{595}$$^1$ | % referred to solvent control |
|---|---|---|---|---|---|
| — | 0.0 | 546.4$^2$ | 100 | 679.5$^2$ | 100 |
| — | 1.0 | 438.5 | 80 | 925.0 | 136 |
| — | 10.0 | 472.8 | 87 | 971.4 | 143 |
| — | 100.0 | 242.5 | 44 | 322.0 | 47 |
| — | 1000.0 | 98.0 | 18 | 134.6 | 20 |
| — | 0.0 | 593.1 | 100 | 549.8 | 100 |
| 50.0 | 0.0 | 1108.6 | 187 | 1171.4 | 213 |
| 50.0 | 1.0 | 601.0 | 101 | 1200.4 | 218 |
| 50.0 | 10.0 | 748.2 | 126 | 1109.3 | 202 |
| 50.0 | 100.0 | 497.4 | 84 | 367.9 | 67 |
| 50.0 | 1000.0 | 118.8 | 20 | 160.5 | 29 |
| — | 0.0 | 1296.9 | 100 | 952.0 | 100 |
| 300.0 | 0.0 | 778.8 | 60 | 824.9 | 87 |
| 300.0 | 1.0 | 905.3 | 69 | 1306.4 | 137 |
| 300.0 | 10.0 | 841.9 | 65 | 1224.7 | 129 |
| 300.0 | 100.0 | 363.7 | 28 | 451.2 | 47 |
| 300.0 | 1000.0 | 123.7 | 10 | 145.9 | 15 |
| — | 0.0 | 1298.1 | 100 | 2008.8 | 100 |
| 50.0* | 0.0* | 852.6 | 66 | 776.2 | 39 |
| 50.0* | 1.0* | 652.1 | 50 | 809.9 | 40 |
| 50.0* | 10.0* | 583.9 | 45 | 1343.1 | 67 |

TABLE 3-continued

Main experiment: Protein Synthesis

| | | Experiment I | | Experiment II | |
|---|---|---|---|---|---|
| SB16-WG779 [μg/ml] | cisplatin [μg/ml] | $^3$H/OO$_{595}$[1] | % referred to solvent control | $^3$H/OO$_{595}$[1] | % referred to solvent control |
| 50.0* | 100.0* | 295.3 | 23 | 298.3 | 15 |
| 50.0* | 1000.0* | 118.1 | 9 | 172.2 | 9 |
| — | 0.0 | 688.2 | 100 | 483.4 | 100 |
| 300.0* | 0.0* | 737.2 | 107 | 1427.5 | 295 |
| 300.0* | 1.0* | 1586.9 | 230 | 1509.1 | 312 |
| 300.0* | 10.0* | 680.7 | 99 | 1427.5 | 295 |
| 300.0* | 100.0* | 395.4 | 58 | 295.0 | 61 |
| 300.0* | 1000.0* | 136.9 | 10 | 148.9 | 31 |

[1] = specific protein synthesis, average value of 3 cultures
[2] = average value of 6 cultures
* = 24 h. pretreatment with SB16-WG779 + 1 h. co-incubation with SB16-WG779 and cisplatin
SB16-WG779 = silibinin-C-2',3-dihydrogen succinate disodium salt (silibinin dihemisuccinate)

We claim:

1. A method for treatment or prophylaxis of a subject with a tumor, comprising administering to said subject an anti-tumor agent, a flavolignant adjuvant which does not promote proliferating tumor cells, and at least one alkali metal citrate of formula:

$K_W N_X H_Y (C_6 H_5 O_7) Z$ wherein W and X are whole numbers from 0 to 15, Y is a whole number from 0 to 3, Z is a whole number from 1 to 5, wherein (W+X+Y) and Z stand in a 3:1 ratio, and W+X adds up to a whole number from 1 to 15.

2. Composition useful in tumor, therapy comprising at least one anti-tumor against a flavolignan adjuvant which does not promote proliferation of tumor cells and a compound of formula:

$K_W N_X H_Y (C_6 H_5 O_7) Z$ wherein W and X are whole numbers from 0 to 15, Y is a whole number from 0 to 3, Z is a whole number from 1 to 5, wherein (W+X+Y) and Z stand in a 3:1 ratio, and W+X adds up to a whole number from 1 to 15.

* * * * *